US005942423A

United States Patent [19]
Demain et al.

[11] Patent Number: 5,942,423
[45] Date of Patent: *Aug. 24, 1999

[54] CONVERSION OF COMPACTIN TO PRAVASTATIN BY ACTINOMADURA

[75] Inventors: Arnold L. Demain, Wellesley; Yulin Peng, Cambridge, both of Mass.; Jacob Yashphe, Mevasseret-Zion, Israel; Joseph Davis, Azle, Tex.

[73] Assignee: Massachusetts Institute of Technology, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/485,711

[22] Filed: Jun. 7, 1995

[51] Int. Cl.$^6$ ....................................... C12P 17/06
[52] U.S. Cl. ........................... 435/125; 435/136; 435/146
[58] Field of Search ..................................... 435/125, 136, 435/146

[56] References Cited

U.S. PATENT DOCUMENTS

| | | |
|---|---|---|
| 4,346,227 | 8/1982 | Terahara et al. . |
| 4,410,629 | 10/1983 | Terahara et al. . |
| 4,448,979 | 5/1984 | Terahara et al. . |
| 4,537,859 | 8/1985 | Terahara et al. . |
| 5,179,013 | 1/1993 | Matsuoka et al. . |

FOREIGN PATENT DOCUMENTS

| | | |
|---|---|---|
| 1150170 | 7/1983 | Canada . |
| 1186647 | 5/1985 | Canada . |

OTHER PUBLICATIONS

N. Serizawa, et al., "6α–Hydroxy–ISO–ML–236B (6α–Hydroxy–ISO–Compactin) and ML–236A, Microbial Transformation products of ML–236B", J. Antibiotics 36(7):918–920 (1983).

Y. Tsuhita et al., "CS–514, a competitive inhibitor of 3–hydroxy–3–methylglutaryl coenzyme A reductase: tissue– selective inhibition of sterol synthesis and hypolipidemic effect on various animal species", Biochimica et Bipphysica Acta 887:50–60 (1986).

M. Hosobuchi et al., "Morphology Control of Preculture during Production of ML–236B, a Precursor of Pravastating Sodium, by *Penicillium citrinum*", J. Fermentation and Bioengineering 76(6):476–481 (1993).

N. Serizawa et al., "Microbial Hydroxylation of ML–236B (Compactin) and Monacolin K (MB–530B0", J. Antibiotics 36(5):604–607 (1983).

N. Serizawa and T. Matsuoka, "A two component–type cytochrome P–450 monooxygenase system in a prokaaryote that catalyzes hydroxylation of ML–236B to pravastatin, a tissue–selective inhibitor of 3–hydroxy–3–methylglutaryl coenyme A reductase", Biochimica et Biophysica Acta 1084:35–40 (1991).

N. Serizawa et al., "3α–Hydroxy–ML–236B (3α–Hydroxycompactin), Microbial Transformation Product of ML–236B (Compactin)", J. Antibiotcs 36(5):608–610 (1983).

T. Fujioka et al., "The mechanism of lack of hypocholesterolemic effects of pravastatijn sodium, a 3–hydroxy–3–methylglutaryl coenzyme A reductase inhibitor, in rats", Biochimica et Biophysica Acta 1254:7–12 (1995).

M. Hosobuchi et al., "Fuzzy Control in Microbial Production of ML–236B, a Precursor of Pravastatin Sodium", J. Fermentation and Bioengineering 76(6):482–486 (1993).

N. Serizawa et al., "Microbial Hydroxylation of ML–236B (Compactin) Studies on Microorganisms Capable of 3β–Hydroxylation of ML–236B", J. Antibiotics 36(7):887–891 (1983).

T. Matsuoka et al., "Purification and Characterization of cytochrome P–450$_{sca}$ from *Streptomyces carbophilus*", Eur. J. Biochem 184:707–713 (1989).

Y. Kishida et al., "Reasearch and Development of Pravastatin", Yakugaku Zasshi 111(9):469–487 (1991).

M. Hosobuchi et al. "Application of Computer to Monitoring and Control of Fermentation Process: Microbial Conversion of ML–236B Na to Pravastatin", Biotechnology and Bioengineering 42:815–820 (1993).

F. Nara et al., "Development of a transformation system for the filamentous, ML–236B (compactin) – producing fungus *Pencillium citrinum*", Curr. Genet 23:28–32 (1993).

H. Yamashita et al., "Microbial Hydroxylation of Compactin (ML–236B) and Monacolin K", 38(5):605–609 (1985).

M. Hosobuchi et al., "Morphology Study in Production of ML–236B, a Precursor o Pravastatin Sodium, by *Penicillium citrinum*", J. Fermentation and Bioengineering 76(6):470–475 (1993).

M.A. Wallace et al., "The Synthesis of Carbon–14 Labeled Pravastating", J. Labelled Compounds and Radiopharmaceuticals 33(8):697–702 (1993).

A. Endo et al., "The Synthesis of Compactin (ML–236B) and Monacolin K in Fungi", J. Antibiotics, 39(11):1609–1610 (1986).

*Primary Examiner*—Herbert J. Lilling
*Attorney, Agent, or Firm*—Testa Hurwitz & Thibeault LLP

[57] ABSTRACT

A method for converting compactin to pravastatin is described. Compactin is provided and contacted with an agent derived from Actinomadura under conditions in which the agent converts compactin to pravastatin. Also described are an Actinomadura strain, an Actinomadura cell free extract, an Actinomadura hydroxylase, and a method for lowering cholesterol levels in mammals.

25 Claims, No Drawings

CONVERSION OF COMPACTIN TO PRAVASTATIN BY ACTINOMADURA

FIELD OF THE INVENTION

This invention relates to methods for converting compactin to pravastatin using an agent derived from the filamentous bacterium Actinomadura, to methods for lowering cholesterol levels in mammals, and to Actinomadura and to Actinomadura hydroxylase.

BACKGROUND OF THE INVENTION

One of the major causes of atherosclerosis and coronary disease is attributed to high blood cholesterol levels. It has been estimated that at least about 50% of total body cholesterol is derived from de novo cholesterol synthesis. A major rate-limiting step in the cholesterol biosynthetic pathway is catalyzed by 3-hydroxy-3-methylglutaryl (HMG)-CoA reductase. Compactin and pravastatin have been reported to be competitive inhibitors of HMG-CoA reductase, and the presence of either one can result in inhibition of cholesterol biosynthesis.

Microbial hydroxylation of compactin can produce hydroxylated forms of compactin, e.g., pravastatin. Some hydroxylated forms are reportedly more effective than compactin as competitive inhibitors of HMG-CoA. It has been reported that this hydroxylation can be effected to differing degrees by many different genera of fungi, and from the bacteria Nocardia and *Streptomyces roseochromogenus* and *Streptomyces carbophilus*. See, e.g., U.S. Pat. No. 5,179,013; U.S. Pat. No. 4,448,979; U.S. Pat. No. 4,346,227; U.S. Pat. No. 4,537,859; Canadian Patent No. 1,150,170; Canadian Patent No. 1,186,647; Serizawa et al., J. Antibiotics 36: 887–891 (1983).

A problem with using fungi for the production of pravastatin is that they generally do not tolerate increases in the amount of compactin added to the culture medium, presumably due to the anti-fungal activity of compactin. Serizawa et al., J. Antibiotics 36: 887–891 (1983).

The cytochrome P450 system has been shown to be required for the hydroxylation of compactin to pravastatin in Streptomyces carbophilus. Matsuoka et al., Eur. J. Biochem. 184: 707–713 (1989). Problems with the use of such an enzyme is that it is a complex of proteins rather than a single protein, making recombinant DNA manipulations difficult, and that compactin, which is an inducer of the cytochrome P450 system, is very expensive.

SUMMARY OF THE INVENTION

It is an object of the invention to provide an effective and relatively inexpensive method for converting compactin to pravastatin.

It is another object of the invention to use Actinomadura, a filamentous bacterium, to convert compactin to pravastatin.

It is yet another object of the invention to use an Actinomadura hydroxylase to convert compactin to pravastatin.

It is yet another object of the invention to use an Actinomadura constitutive hydroxylase that does not require compactin as an inducer, to convert compactin to pravastatin.

Still another object of the invention is to use pravastatin, derived from an Actinomadura hydroxylase that converts compactin to pravastatin, to treat a mammal so as to lower the mammal's blood cholesterol level.

According to the invention, a method for converting compactin to pravastatin is provided. Compactin is provided and contacted with an agent, e.g., a hydroxylation enzyme, e.g., a hydroxylase that is, e.g., constitutive and cytochrome P450 system-independent, derived from Actinomadura, under conditions in which the agent converts compactin to pravastatin. In certain embodiments, the pravastatin is isolated.

Preferably, the compactin is provided by providing, e.g., a microorganism, e.g., a fungus or bacterium, that produces compactin, or a cell free extract of a microorganism that produces compactin, or cell free culture media from a pregrown culture of a microorganism that produces compactin, or a solution comprising compactin, or semi-purified compactin, or substantially purified compactin.

In certain embodiments, the compactin is contacted with the agent, e.g., by contacting whole cells of Actinomadura with the compactin, or by contacting a cell free extract of Actinomadura with the compactin, or by contacting cell free culture media from a pregrown culture of Actinomadura with the compactin, or by contacting a solution having the Actinomadura agent with the compactin, or by contacting semi-purified or substantially purified Actinomadura agent with the compactin.

Variations include, e.g., contacting, e.g., a culture, e.g., a pregrown culture or a starting culture, or a cell free extract, of the microorganism that produces compactin, or semi-purified or substantially purified compactin, with, e.g., a culture, e.g., a pregrown culture or a starting culture, or a cell free extract, of Actinomadura, or semi-purified or substantially purified Actinomadura agent.

Another aspect of the invention is a cell free extract derived from Actinomadura, having an agent, e.g., a hydroxylase, that converts compactin to pravastatin.

Another aspect of the invention is a hydroxylase, e.g., semi-purified or substantially purified, from Actinomadura that converts compactin to pravastatin, wherein the hydroxylase is a constitutive enzyme, wherein the activity of the hydroxylase is stimulated by any of ATP, ascorbic acid or $Mg^{++}$, but not by $Fe^{++}$ or $Fe^{+++}$, and wherein the hydroxylase is cytochrome P450 system-independent.

Another aspect of the invention is purified Actinomadura ATCC 55678 having an agent for converting compactin to pravastatin.

Yet another aspect of the invention is a method for treating a mammal to lower the blood cholesterol level of the mammal. Pravastatin, derived from compactin by contacting the compactin with an agent, e.g., a hydroxylase, derived from Actinomadura that converts compactin to pravastatin, is provided. The pravastatin is administered to a mammal in need of such treatment to cause a lower blood cholesterol level in the mammal.

The above and other objects, features and advantages of the present invention will be better understood from the following specification.

DETAILED DESCRIPTION

This invention provides a method for converting compactin to pravastatin. Compactin is provided and contacted with an agent derived from Actinomadura under conditions in which the agent converts compactin to pravastatin. In certain embodiments, the pravastatin is isolated.

Compactin (also known as mevastatin, ML-236B, and CS-500) is meant to include, e.g., the acid form (also known as ML-236B carboxylic acid), the lactone form (also known as ML-236B lactone), and salts and esters thereof. The lactone form of compactin may be represented by the formula (I):

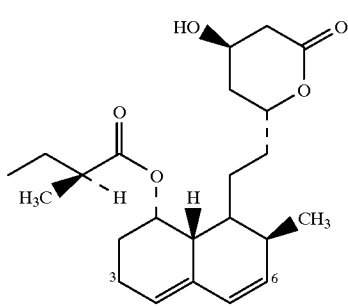

A preferred compactin is the sodium salt of compactin.

Pravastatin (also known as eptastatin, mezalotin, pravachol, CS-514, and SQ-31000) is meant to include, e.g., the acid form, the lactone form, and salts and esters thereof. The 3β-hydroxy lactone form of pravastatin may be represented by the formula (II):

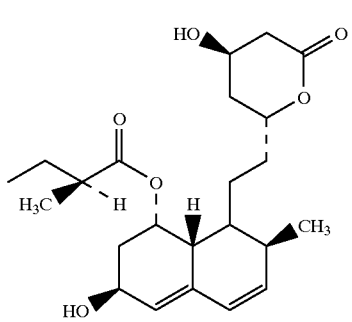

Other forms of hydroxylated compactin include compounds in which the hydroxyl group is added at other positions of the compactin molecule, e.g., at position 6.

The compactin can be provided in any way which enables the agent to act upon it. For example, compactin can be provided by providing a microorganism, e.g., a fungus or bacterium, that produces compactin. Microorganism is meant to include, e.g., microbial cells which are intact, immobilized or permeabilized. Production of compactin by the microorganism is meant to include the microorganism using its own natural gene or genes, or fragments thereof, to produce the compactin, and/or the microorganism using a foreign gene or genes, or fragments thereof, to produce the compactin. The foreign gene can be introduced into the microorganism by standard molecular cloning techniques known in the art, or by any other means which will result in expression of the compactin producing gene or genes, or fragments thereof, in the microorganism. In certain embodiments, the compactin is provided by using a cell free extract of a microorganism that produces compactin. The cell free extract can be prepared by a variety of methods known in the art, e.g., by physical or chemical means, so as to rupture the cells. Such methods include, e.g., grinding, ultrasonic treatment, or treatment with an enzyme or surface active agent. Preferably, the cell free extract is prepared with a French Press. Cell free extract is meant to include the material resulting from any of the preparation methods, or the soluble fraction resulting from any of the preparation methods. Preferably, the cell free extract comprises essentially the cellular contents without the particulate cellular debris, e.g., walls, e.g., wherein the walls have been essentially removed. Cell free extracts can be made from cells obtained before, during or after active growth of the cells. In other embodiments, the compactin can be provided by providing cell free culture media from a pregrown culture of a microorganism that produces compactin. In other embodiments, the compactin can be provided by providing a solution comprising compactin. In yet other embodiments, the compactin can be provided by using semi-purified or substantially purified compactin. The compactin can be free or immobilized. Any other source of compactin can be used in this invention. Compactin can be used in this invention at any concentration which will result in production of pravastatin. Preferably, the compactin concentration is between about 0.1 and about 100 g/liter, more preferably is between about 0.2 and about 25 g/liter, and most preferably is between about 1 and about 10 g/liter. In some embodiments, the compactin is added to the Actinomadura agent in shots. By shots is meant sequential additions of the agent. See Example 3.

The compactin is contacted with an agent derived from Actinomadura. Actinomadura is a genus belonging to the filamentous bacteria, actinomycetes. Actinomadura is meant to include wild type or any mutants which possess the ability to convert compactin to pravastatin. The mutants can be derived, e.g., spontaneously, or from physical agents, e.g., ultraviolet radiation, high frequency electromagnetic waves or nuclear radiation, or chemical agents, or from genetic engineering techniques.

Morphological and chemotaxonomic properties of a newly isolated strain included in this invention were compared with those of similar taxa and the results showed that the strain belongs to the genus Actinomadura. Deposit of these Actinomadura cells (strain 2966) has been made on Jun. 1, 1995, with the American Type Culture Collection, 12301 Parklawn Drive, Rockville, Md. 20852, and has been assigned deposit number ATCC 55678.

The agent derived from Actinomadura is meant to include, e.g., an enzyme, e.g., a hydroxylation enzyme, e.g., a hydroxylase, or any active portion thereof, that is able to convert compactin to pravastatin. The Actinomadura agent can be made in vivo or in vitro, e.g., in cell-free systems or by chemical synthesis. The agent includes wild type and mutated forms. The mutated agents can be derived spontaneously or from mutating the Actinomadura, e.g., with physical or chemical agents, or from utilizing genetic engineering techniques known to those skilled in the art. Mutated agents can also be synthesized by chemical techniques known to those skilled in the art. The agent is also meant to include, e.g., an agent derived from a genetically engineered strain of Actinomadura in which the nucleic acid coding for the agent or any active portion thereof, is operatively connected to a regulatory region, or portion thereof, that is different from the wild type regulatory region for the agent. In certain embodiments, the nucleic acid coding for the Actinomadura agent is cloned into another type of cell, e.g., a bacterium, e.g., *Escherichia coli, Bacillus subtilis, Bacillus brevis* or *Streptomyces lividans;* a fungus, e.g., *Saccharomyces cerevisiae, Pichia pastoris, Hansenula polymorpha;* insect cells; transgenic plants; or transgenic animals. In a preferred embodiment, the Actinomadura agent is cloned into a microorganism which is able to produce compactin, e.g., with the microorganism's own gene(s), or with foreign gene(s).

The agent of this invention is a constitutive enzyme, and therefore does not require induction with compactin. See Example 6. $Mg^{++}$, ATP and ascorbic acid, alone or in combination, but not $Fe^{++}$ or $Fe^{+++}$, stimulates the enzymatic activity of the agent. See Example 8. Preferably, NADPH is used as a $H^+$ donor, though NADH or other $H^+$ donors can be used. Cofactors, e.g., α-ketoglutarate, $CoCl_2$, $NiCl_2$, $CuSO_4$, FMN or FAD, do not stimulate enzymatic activity of the agent. The agent is cytochrome P450 system-independent. See Example 7.

The compactin can be contacted with the agent in any way which enables the agent to convert the compactin to pravastatin. For example, the compactin can be contacted with whole cells of Actinomadura, or with a cell free extract of Actinomadura, or with cell free culture media from a pregrown culture of Actinomadura, or with a solution comprising the Actinomadura agent, or with semi-purified or substantially purified Actinomadura agent.

In certain embodiments, a pregrown culture of a microorganism that produces compactin is contacted with a pregrown culture of Actinomadura. By pregrown culture is meant a culture which has been inoculated with cells and cultured for some period of time, preferably about 1 to about 8 days, more preferably about 1 to about 5 days, and most preferablby about 2 to about 4 days. In other embodiments, a pregrown culture of a microorganism is contacted with a starting culture of Actinomadura. By starting culture is meant a culture which is inoculated with cells from, e.g., a slant culture, a frozen culture, a lyophilized culture or a liquid seed culture. In other embodiments, a starting culture of a microorganism that produces compactin is contacted with a pregrown culture of Actinomadura. In other embodiments, a starting culture of a microorganism that produces compactin is contacted with a starting culture of Actinomadura. This mixture of cultures is grown for some period of time, preferably about 0.5 to about 8 days, more preferably about 1 to about 5 days, and most preferably about 2 to about 4 days.

In other embodiments, a cell free extract of a microorganism that produces compactin is contacted with a culture, e.g., starting or pregrown, of Actinomadura. In other embodiments, a culture, e.g., starting or pregrown, of a microorganism that produces compactin is contacted with a cell free extract of Actinomadura. And, in yet other embodiments, a cell free extract of a microorganism that produces compactin is contacted with a cell free extract of Actinomadura. In other embodiments, a culture, e.g., starting or pregrown, of a microorganism that produces compactin is contacted with a cell free extract of Actinomadura. Combinations using semi-purified or substantially purified compactin, or semi-purified or substantially purified Actinomadura agent are also included in this invention.

The conversion reaction of compactin to pravastatin can be done using any conditions which will result in the production of pravastatin. Any method of cultivation can be used, e.g., fermentation techniques, e.g., batch culture, fed-batch culture, continuous or solid-state culture. Preferably, an agitated liquid submerged culture is used, most preferably of the type useful for large scale industrial fermentation. Additives can be used during growth which contribute to the development of the hydroxylating system within the cells.

The preferred temperature is about 18° C. to about 50° C., more preferably about 25° C. to about 37° C., and most preferably about 28° C. to about 31° C. The preferred pH is about 5 to about 10, more preferably about 6 to about 8.5, and most preferably about 7.2 to about 8.0. Preferably, aerobiosis is provided, e.g., by agitation and/or aeration. The preferred shaking condition is about 0 rpm to about 400 rpm, more preferably about 200 rpm to about 250 rpm, and most preferably about 220 rpm.

The invention is meant to cover any percentage of conversion of compactin to pravastatin by the Actinomadura agent, preferably at least about 10%, more preferably at least about 25%, more preferably yet at least about 40%, more preferably yet at least about 50%, more preferably yet at least about 60%, more preferably yet at least about 70%, and most preferably at least about 80%. The percentage conversion is calculated by dividing the concentration of pravastatin by the concentration of compactin charged (initially added) and multiplying by 100.

In preferred embodiments, the pravastatin is isolated. Isolated is meant to include, e.g., enriched, separated or purified. Isolation can be by any method known to those skilled in the art, including, e.g., precipitation; extraction, e.g., with a solvent, e.g., ethyl acetate or butanol, and removal of the solvent, e.g., by distillation; chromatography, e.g., thin layer chromatography or column chromatography, e.g., using a matrix, e.g., alumina or silica gel, followed by elution. A preferred chromatographic method includes, e.g., high pressure liquid chromatography (HPLC). See, e.g., Serizawa et al., J. Antibiotics (1983).

The invention also includes a cell free extract from Actinomadura that has an agent, e.g., a hydroxylase, that converts compactin to pravastatin. The cell free extract can be obtained by any method, including those described above. Preferably, the cell free extract comprises essentially the cellular contents without particulate cellular debris, e.g., walls, e.g., wherein the walls have been essentially removed. Preferably, conversion of compactin to pravastatin by the cell free extract is at least about 10%, more preferably at least about 25%, more preferably yet at least about 40%, more preferably yet at least about 50%, more preferably yet at least about 60%, more preferably yet at least about 70%, and most preferably at least about 80%.

The invention also includes a hydroxylase, e.g., semi-purified or substantially purified, from Actinomadura that converts compactin to pravastatin. The hydroxylase is a constitutive enzyme. The activity of the hydroxylase is stimulated by any of ATP, ascorbic acid and $Mg^{++}$, or by combinations thereof, but not by $Fe^{++}$ or $Fe^{+++}$. Preferably, NADPH is used as a $H^+$ donor, though NADH or other $H^+$ donors can be used. Cofactors, e.g., α-ketoglutarate, $CoCl_2$, $NiCl_2$, $CuSo_4$, FMN or FAD, do not stimulate the activity of the hydroxylase. The hydroxylase is cytochrome P450 system-independent.

The invention also includes Actinomadura ATCC 55678, having an agent, e.g., a hydroxylase, for converting compactin to pravastatin.

The invention further includes a method for treating a mammal to lower the blood cholesterol level of the mammal. Pravastatin, derived from compactin by contacting the compactin with an agent, e.g., a hydroxylase, derived from Actinomadura that converts compactin to pravastatin, is provided. The pravastatin is administered to a mammal in need of such treatment to cause a lower blood cholesterol level in the mammal.

By mammal is meant human as well as non-human mammals. Treating a mammal to lower blood cholesterol levels is meant to include, e.g., preventing or lowering high blood cholesterol levels.

Administration of the pravastatin can be accomplished by any method which allows the pravastatin to reach its target. By target is meant the place where the pravastatin is able to inhibit the cholesterol biosynthetic pathway in the mammal. The administration methods include, e.g., injection, deposition, implantation, suppositories, oral ingestion, inhalation, topical administration, or any other method of administration where access to the target by pravastatin is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses, e.g., pills, can be enterically coated. Inhalation includes administering pravastatin with an aerosol in an inhalator, either alone or attached to a carrier that can be absorbed.

The pravastatin can be suspended in a liquid, e.g., in dissolved form or colloidal form. The liquid can be a solvent, partial solvent or non-solvent. In many cases, water or an organic liquid can be used. Administration of pravastatin can be alone or in combination with other therapeutic agents. In certain embodiments, the pravastatin can be combined with a suitable carrier, e.g., a pharmaceutically acceptable carrier. In certain embodiments, the pravastatin is incorporated into a liposome or incorporated into a polymer release system.

In certain embodiments of the invention, the administration can be designed so as to result in sequential exposures to the pravastatin over some time period, e.g., hours, days, weeks, months or years. This can be accomplished by repeated administrations of the pravastatin by one of the methods described above, or alternatively, by a controlled release delivery system in which the pravastatin is delivered to the mammal over a prolonged period without repeated administrations. Administration of such a system can be, e.g., by long acting oral dosage forms, bolus injections, transdermal patches and sub-cutaneous implants.

The pravastatin can be administered prior to or subsequent to the appearance of high blood cholesterol levels. In certain embodiments, the pravastatin is administered to subjects who have a family history of high blood cholesterol levels, or who have a genetic predisposition for this condition. In other embodiments, the pravastatin is administered to subjects who have reached a particular age and who, therefore, are more likely to be affected by high blood cholesterol levels. In yet other embodiments, the pravastatin is administered to subjects who exhibit either early or advanced symptoms of the condition. The pravastatin can also be administered as a preventive measure.

The pravastatin is administered to the mammal in a therapeutically effective amount. By therapeutically effective amount is meant that amount which is capable of at least partially preventing or reversing high blood cholesterol levels. A therapeutically effective amount can be determined on an individual basis and will be based, at least in part, on consideration of the species of mammal, the mammal's size, the type of delivery system used, the time of administration relative to the level of blood cholesterol, and whether a single, multiple, or controlled release dose regimen is employed. A therapeutically effective amount can be determined by one of ordinary skill in the art employing such factors and using no more than routine experimentation.

Preferably, the dosage of pravastatin for a human is about 0.1 to about 5000 mg/day, more preferably it is about 1 to about 500 mg/day, and most preferably it is about 10 to about 50 mg/day. Preferably, the dosage form is such that it does not substantially deleteriously affect the mammal.

EXAMPLES

Example 1

Bioconversion of Compactin to Pravastatin by Intact Cells of Actinomadura

This example illustrates the bioconversion of compactin to pravastatin by Actinomadura cells. Actinomadura ATCC 55678 was grown in YM medium (yeast extract 3 g, malt extract 3 g, peptone 5 g, glucose 10 g, per liter, pH 6.5) for 48 hours, at 28° C., with shaking at 220 rpm. 500 μg/ml Na compactin (obtained from Fluka Chemical Corp., New York, N.Y.) was then added. The Actinomadura cultures were further incubated in the same medium for 1, 2, 3, 4 or 5 days. At the end of each of these time periods, the amount of compactin (CP) and pravastatin (PV) was determined by high performance liquid chromatography (HPLC).

The HPLC conditions used were a 3 μm Lichrospher 100 RP-18 column (obtained from EM Separations Technology, Gibbstown, N.J.); Mobile Phase A: 2.5 g $NaH_2PO_4$ in 800 ml Milli-Q water, add 200 ml acetonitrile and 110 ml methanol, adjust pH to 2.5 with 85% $H_3PO_4$; Mobile Phase B: mixture of 200 ml water, 800 ml acetonitrile, 110 ml methanol and 1 ml 85% $H_3PO_4$; a 10 μl injection volume; a 1 ml/min. flow rate; and detection at UV 237 nm. The gradient table was:

| Time (min.) | A% | B% | Curve |
|---|---|---|---|
| 0 | 90 | 10 | * |
| 5 | 90 | 10 | 11 |

-continued

| Time (min.) | A% | B% | Curve |
|---|---|---|---|
| 35 | 20 | 80 | 6 |
| 40 | 90 | 10 | 6 |
| 55 | 90 | 10 | 11 |

The HPLC results are shown in Table 1. PV is pravastatin; CP is compactin.

TABLE 1

Bioconversion by Actinomadura During 5 Days Incubation

| days | 1 | 2 | 3 | 4 | 5 |
|---|---|---|---|---|---|
| PV | 252 | 262 | 290 | 318 | 326 |
| CP | 32 | 0 | 0 | 0 | 5.4 |
| % conversion | 50.4 | 52.4 | 58.0 | 63.6 | 65.2 | unit: μg/ml

% conversion was calculated on the basis of compactin charged, not compactin used (the compactin was weighed before addition, but the charge was determined by HPLC assay at time zero).

Example 2

Kinetics of Bioconversion of Compactin to Pravastatin by Intact Cells of Actinomadura This example illustrates the kinetics of the bioconversion of compactin to pravastatin by Actinomadura. A culture medium containing 2% glucose, 0.5% peptone, 0.3% yeast extract and 0.3% malt extract was prepared and adjusted to pH 5.5. Erlenmeyer flasks of 250 ml volume, each of which contained 20 ml of the medium, were sterilized at 121° C. for 15 minutes. Each volume was then inoculated with a platinum loop containing cells of Actinomadura ATCC 55678 from a slant culture, and then cultured with shaking at 250 rpm, 28° C. for 5 days. This procedure resulted in a suspension containing pellets plus turbid liquid. 2 ml of the turbid part of the culture was inoculated into another 250 ml Erlenmeyer flask with 20 ml medium and incubated shaking at 250 rpm, 28° C. for 2 days, giving a seed culture. 50 ml aliquots of the above medium were added to 500 ml Erlenmeyer flasks, and sterilized at 121° C. for 15 minutes. 5 ml of seed culture was added into each flask. After 2 days, compactin was added into each flask to a level of 500 μg/ml and further cultured for 36 hours. The rate of pravastatin production at different time intervals during 36 hours of bioconversion was determined as described in Example 1. The results are shown in Table 2.

TABLE 2

Bioconversion by Actinomadura During 36 Hours Incubation

| Time (hours) | 0 | 4 | 8 | 12 | 17 | 20 | 24 | 30 | 33 | 36 |
|---|---|---|---|---|---|---|---|---|---|---|
| PV | 0 | 62.7 | 109 | 158 | 205 | 224 | 238 | 258 | 263 | 274 |
| CP | 502 | 390 | 301 | 209 | 111 | 79.2 | 84.9 | 55.3 | 46.2 | 6.9 |
| % conversion | 0 | 12.5 | 21.7 | 31.5 | 40.8 | 44.6 | 47.4 | 51.4 | 52.4 | 54.6 | unit: μg/ml

For 16 hours both pravastatin production and compactin consumption were linear.

Additional experiments were conducted to examine bioconversion at shorter time intervals over 7 hours, at compactin concentrations of 200 μg/ml and 500 μg/ml. The results are shown in Tables 3 and 4.

TABLE 3

200 μg/ml Compactin

| Time (hours) | 0 | 0.5 | 1 | 2 | 3 | 4 | 5 | 6 | 7 |
|---|---|---|---|---|---|---|---|---|---|
| PV | 0 | 3.5 | 6.5 | 12.7 | 18.8 | 24.5 | 28.8 | 33 | 48.7 |
| CP | 227 | 199 | 194 | 184 | 174 | 163 | 156 | 152 | 130 |
| % conversion | 0 | 1.5 | 2.9 | 5.6 | 8.3 | 10.8 | 12.7 | 14.5 | 21.5 | unit: μg/ml

TABLE 4

500 μg/ml Compactin

| Time (hours) | 0 | 0.5 | 1 | 2 | 3 | 4 | 5 | 6 | 7 |
|---|---|---|---|---|---|---|---|---|---|
| PV | 0 | 3.6 | 6.8 | 13.2 | 18.9 | 24.5 | 28.9 | 32.6 | 54.1 |
| CP | 494 | 493 | 488 | 477 | 466 | 459 | 455 | 452 | 430 |
| % conversion | 0 | 0.6 | 1.4 | 2.7 | 3.8 | 5.0 | 5.9 | 6.6 | 11 | unit: μg/ml

From the above results, it is clear that there was essentially no difference between the two compactin concentrations in the rate of pravastatin production.

Example 3

Bioconversion of Compactin to Pravastatin by Intact Cells of Actinomadura When the Compactin is Added in Shots This example illustrates that the pravastatin concentration resulting from the bioconversion of compactin to pravastatin by intact cells of Actinomadura is increased if the compactin is added in shots. Actinomadura ATCC 55678 was grown as described in Example 2, with 500 μg/ml compactin added as described. An additional 300 μg/ml compactin was added at the first day, and yet another additional 300 μg/ml compactin was added at the second day. The amounts of compactin and pravastatin were measured as described in Example 1. The results are shown in Table 5.

TABLE 5

Bioconversion by Actinomadura With Compactin Added in Shots

| Time (days) | 0 | 1 | 1 (after CP added) | 2 | 2 (after CP added | 3 | 4 | 5 | 6 | 7 |
|---|---|---|---|---|---|---|---|---|---|---|
| PV | 0.8 | 271 | 258 | 398 | 380 | 479 | 536 | 585 | 684 | 821 |
| CP | 481 | 0 | 304 | 37.0 | 299 | 146 | 85.5 | 69.7 | 64.7 | 78.0 |
| total added CP | 481 | | 785 | | 1047 | | | | | |
| % conversion | | 57.3 | | 50.7 | | 46.0 | 51.2 | 55.9 | 65.3 | 78.4 | unit: μg/ml

The results indicate that very high concentrations of pravastatin (821 μg/ml) were obtained after 7 days when the compactin was added in shots. Experiments conducted under similar conditions except for compactin being added only once (no shots), gave lower concentrations of produced pravastatin. In addition, as shown in Table 5, the percent bioconversion was increased to 78% in the shots experiment. Thus, adding compactin in shots led to higher pravastatin concentrations and higher percent conversion. The rate of bioconversion of the compactin to pravastatin was not increased.

Example 4

Growth and Bioconversion of Compactin to Pravastatin by Cells of Actinomadura Grown in Defined Media This example illustrates that a defined medium supports Actinomadura growth and is more efficient for the bioconversion of compactin to pravastatin than complex medium. The chemically-defined medium, denoted Medium A, contains the following:

| | grams/liter |
|---|---|
| sucrose | 30 |
| $NaNO_3$ | 2 |
| $K_2HPO_4$ | 1 |
| $MgSO_4 \cdot 7H_2O$ | 0.5 |
| KCl | 0.5 |
| $FeSO_4$ | 0.01 |
| pH adjusted 7.2 | |

Actinomadura ATCC 55678 was grown for 45 hours in medium A and in complex YM medium (yeast extract 3 g, malt extract 3 g, peptone 5 g, glucose 10 g, per liter, pH 6.5), 5 ml/250 ml flask, at 28° C. with shaking at 220 rpm. Compactin (250 μg/ml) was added at 45 hours. Incubation proceeded for 8 hours. The biomass was then measured, and it was about 25% less for cells grown in Medium A than for cells grown in YM medium. Depsite fewer cells, biocon version of compactin to pravastatin was higher for cells grown in Medium A than for cells grown in YM medium. In YM there was 6.7% conversion; in Medium A there was 13% conversion.

Example 5

Enzymatic Conversion of Compactin to Pravastatin by Cell Free Extracts of Actinomadura Depends on NADPH This example illustrates that cell free extracts of Actinomadura convert compactin to pravastatin, and that NADPH is a better $H^+$ donor than NADH for this enzymatic conversion.

A cell free extract of Actinomadura was obtained by growing a 150 ml culture of Actinomadura ATCC 55678 for 2 days in YM medium as described in Example 1. The cells were harvested by centrifugation at 15,000 rpm for 30 min. Cells were resuspended in 20 ml fresh YM medium, Na compactin was added to about 500 μg/ml and incubated at 29° C., 220 rpm for 3 hours. During this period, 196 μg/ml compactin disappeared and 70 μg/ml pravastatin appeared. Cells were harvested by centrifugation, washed twice with cold water and once with buffer A (80 mm Tris-HCl buffer, pH 7.4, supplemented with 20% glycerol and 2 mM DTT). The cells were resuspended in 5 ml buffer A and stored at −80° C. The cell suspension was later thawed and disrupted in a French Press. The homogenate was centrifugated at 30,000 rpm for 60 min. The supernatant was stored at −80° C. as cell free extract.

The reaction conditions were: 160 μl cell free extract, 0.26 mM NADH or NADPH, 0.23 mM compactin, 220 μl total volume, 30° C., 250 rpm. A control of buffer A without cell free extract was included. The amount of pravastatin was measured by HPLC as described in Example 1. The results are shown in Table 6.

TABLE 6

Comparison of NADH and NADPH as $H^+$ Donors in Conversion by Cell Free Extracts of Actinomadura

| | NADH | | NADPH | | control | |
|---|---|---|---|---|---|---|
| time (hours) | 5 | 21 | 6 | 21 | 6 | 22 |
| PV (μg/ml) | 2.8 | 2.8 | 12.8 | 11.9 | 0 | 0 |

The results show that there is enzymatic conversion of compactin to pravastatin by cell free extracts and that it is better with NADPH as a $H^+$ donor than with NADH.

Example 6

Enzymatic Conversion of Compactin to Pravastatin from "Induced" and Uninduced Actinomadura Measured in Cell Free Extracts

This example illustrates that, as measured in cell free extracts, the enzymatic conversion of compactin to pravastatin in Actinomadura does not require induction and that therefore the Actinomadura hydroxylase is a constitutive enzyme.

Cell free extracts were made both from compactin "induced" cells and cells without induction. Actinomadura ATCC 55678 cells were grown for 2 days as described in Example 2, except that the temperature was 29° C., harvested and divided into two flasks. Compactin was then added to one of these flasks at a concentration of about 300 µg/ml (the "induced" culture). Both flasks were incubated at 29° C., 250 rpm for 3 hours. Cells were harvested at this time and cell free extracts were made with a French Press as described in Example 4. The reaction conditions were: 160 µl cell free extract, 0.26 mM NADPH, 0.23 mM compactin, 220 µl total volume, 30° C., 250 rpm, incubated for 60 minutes. Enzyme conversion of the cell-free extract reaction was determined by HPLC as described in Example 1, at 0, 10, 30 and 60 minutes. The results are shown in Table 7.

TABLE 7

Conversion by "Induced" and Uninduced Cell Free Extracts of Actinomadura

|  | Uninduced | | | | "Induced" | | | |
|---|---|---|---|---|---|---|---|---|
| time (min) | 0 | 10 | 30 | 60 | 0 | 10 | 30 | 60 |
| PV. (µg/ml) | 0 | 0.98 | 6.7 | 12.7 | 0 | 2.0 | 5.0 | 9.1 |
| CP (µg/ml) | 97.2 | 77.6 | 69.5 | 68.5 | 90.2 | 80.6 | 67.2 | 56.1 |
| specific rate (µg/min/g protein) | | 18 | | | | 11 | | |

These results indicate that "induction" did not increase the rate of enzymatic conversion. Therefore, the Actinomadura hydroxylase enzyme is a constitutive enzyme.

Example 7

Determination of Cytochrome P450 in Cell Free Extracts of Actinomadura

This example illustrates that the hydroxylase activity of Actinomadura is not a cytochrome P450 enzyme. Cell free extracts of Actinomadura 55678 were prepared as described in Example 5. Preparations 1, 2 and 3 were resuspended in buffer A (80 mM Tris-HCl pH 7.4 supplemented with 2 mM DTT and 20% glycerol) and preparation 4 was resuspended in phosphate buffer. The reaction conditions were: 160 µl cell free extract, 0.26 mM NADPH, 0.23 mM compactin, 220 µl total volume, 30° C., 250 rpm. The hydroxylase activity was measured by HPLC as described in Example 1.

The cytochrome P450 activity was measured as follows. Two milligrams of sodium dithionate were added to 3 ml of cell free extract of Actinomadura ATCC 55678 to reduce P450. The cell free extract was put in a sample cell and a reference cell in a Beckman Model 24 spectophotometer. The absorbance from 400 nm to 500 nm was recorded. The cell free extract in the sample cell was subjected to bubbling with CO for 1 min. to form a P450-CO complex. The spectrum was recorded again. The difference between these two spectra is the P450 difference spectrum.

The P450 content and hydroxylase activity in the different cell free extract preparations are shown in Table 8. The different numbers for the cell free extract (CFE) preparations indicate independent cell free extract preparations.

TABLE 8

Hydroxylase and P450 Specific Activities of Different Cell Free Extract Preparations of Actinomadura

| CFE Prep. | Buffer | Days of Cell Growth | "Induction" | Hydroxylase Activity (mg/min/g prot.) | P450 Peak Height (ABS./g prot.) |
|---|---|---|---|---|---|
| 1 | Buffer A | 4 | + | 13 | 8 |
| 1 | Buffer A | 4 | − | 11 | 2 |
| 2 | Buffer A | 3 | − | 11 | 1 |
| 3 | Buffer A | 2 | + | 15 | 4 |
| 3 | Buffer A | 3 | − | 4.6 | 4 |
| 4 | Phosphate | 2.5 | + | 31 | 3 |
| 4 | Phosphate | 2.5 | − | 10 | 2 |

There was no correlation between the hydroxylase activity and the cytochrome P450 activity. Therefore, the hydroxylase activity derived from Actinomadura is not a cytochrome P450 enzyme.

Example 8

Effect of Various Factors on Conversion of Compactin to Pravastatin in Cell Free Extracts of Actinomadura

This example illustrates that $Mg^{++}$, ATP and ascorbic acid, either alone or in combination, but not $Fe^{++}$ or $Fe^{+++}$, stimulate conversion of compactin to pravastatin in Actinomadura cell free extracts. $Mg^{++}$ is a common cofactor of many enzymes. ATP is a common energy provider for enzymatic reactions. $Fe^{+++}$ and $Fe^{++}$ are in the active site of many oxygenases. Ascorbic acid is a reducing agent often required for oxygenase reactions. The reaction conditions were 160 µl cell free extract, 0.72 mM NADPH, 0.2 mM compactin, 211 µl total volume, 30° C., 250 rpm, 60 min. The factors were added at time zero, at the following concentrations: 2.4 mM $MgCl_2$, 0.09 mM $FeSO_4$, 0.1 mM $FeCl_3$, 1.9 mM ATP and 12 mM ascorbic acid. The results are shown in Tables 9 and 10.

TABLE 9

Effects of $MgCl_2$, $FeSO_4$, $FeCl_3$, ATP and Ascorbic Acid on Cell Free Extracts Derived From Actinomadura

|  | no add. | $MgCl_2$ | $FeSO_4$ | $FeCl_3$ | ATP + ascb |
|---|---|---|---|---|---|
| PV (µg/ml) | 3.2 | 4.4 | 2.3 | 3.3 | 11.3 |
| CP (µg/ml) | 62.4 | 60.2 | 64.3 | 57.9 | 49.9 |
| PV (µg/min/g) | 6.6 | 8.7 | 6.4 | 6.6 | 23 |

TABLE 10

Effects of MgCl$_2$, ATP and Ascorbic Acid on Cell Free Extracts Derived from Actinomadura

|  | CFE Uninduced |  |  |  | CFE "Induced" |  |
|---|---|---|---|---|---|---|
| MgCl$_2$ (mM) | 0 | 2.4 | 0 | 0 | 0 | 2.4 |
| ATP (mM) | 0 | 1.9 | 3.8 | 0 | 0 | 1.9 |
| ascb (mM) | 0 | 12 | 0 | 23 | 0 | 12 |
| PV (μg/ml) | 2.9 | 11.1 | 7.5 | 8.3 | 2.8 | 7.8 |
| CV (μg/ml) | 35.2 | 24.6 | 31.5 | 27.0 | 38.2 | 30.5 |
| PV (μg/min/g) | 6.4 | 24 | 17 | 18 | 7.2 | 20 |

Example 9

Production of Pravastatin by Contacting a Pregrown Culture of Paecilomyces with a Starting Culture of Actinomadura The fungus Paecilomyces sp. M2016 (Endo et al., J. Antibiotics 39: 1609–1610 (1986)), is grown in a medium containing glucose 3.5% starch 1%, soybean meal 2%, meat extract 0.5%, peptone 0.5%, NaCl 0.2%, KH$_2$PO$_4$ 0.05%, and MgSO$_4$.7H$_2$O 0.05%, pH adjusted to 5.8. Erlenmeyer flasks of 250 ml volume, each of which contains 20 ml of the medium, are sterilized at 121° C. for 15 minutes. Each flask is inoculated with a platinum loop of Paecilomyces sp. M2016 from a slant culture, and is cultured with shaking at 250 rpm, 25° C. for 7 days. The compactin produced is detected by HPLC as described in Example 1. The produced compactin is 40 μg/ml. The pH is then adjusted to 7.2. A seed culture of Actinomadura ATCC 55678 is prepared as described in Example 2 and is added into the 7 day culture of Paecilomyces sp. After one day incubation at 28° C., 250 rpm, the pravastatin in the culture is detected by HPLC as described in Example 1. The concentration of pravastatin in the culture is 30 μg/ml.

Example 10

Production of Pravastatin by Contacting a Starting Culture of Paecilomyces with a Cell Free Extract of Actinomadura A culture of the fungus Paecilomyces sp. M2016 is prepared as described in Example 9, except that the culture is mixed immediately after inoculating from the slant culture (without 7 days of pregrowth). A cell free extract of Actinomadura ATCC 55678 is prepared as described in Example 5. The culture of Paecilomyces sp. is adjusted to pH 7.5. 5 ml of the Actinomadura cell free extract is added to 20 ml of the Paecilomyces sp. culture. The mixture is incubated at 30° C., 250 rpm for 2 hours. The pravastatin produced from the compactin is examined by HPLC as described in Example 1. The pravastatin concentration in the culture is 30 μg/ml.

Example 11

Treating High Blood Cholesterol Levels

This example illustrates a method for lowering the cholesterol level in a human with pravastatin derived from an Actinomadura hydroxylase that converts compactin to pravastatin. The patient is given 20 mg of this pravastatin orally, in the form of a pill, twice a day. Administration is carried out for a period of 3 months. This treatment results in a reduction of the patient's blood cholesterol level.

Those skilled in the art will be able to ascertain, using no more than routine experimentation, many equivalents of the specific embodiments of the invention described herein. These and all other equivalents are intended to be encompassed by the following claims.

What is claimed is:

1. A method for converting compactin to pravastin, comprising:
   providing said compactin; and
   contacting said compactin with an agent derived from Actinomadura under conditions in which said agent converts compactin to pravastin, wherein the contacting of said compactin with said agent is selected from the group consisting of contacting whole cells of said Actinomadura, a cell free extract of said Actinomadura prepared by treating whole cells of said Actinomadura so as to rupture said cells, cell free culture media from a pregrown culture of said Actinomadura, and a solution comprising said agent of said Actinomadura, with said compactin.

2. The method of claim 1 further comprising the step of isolating said pravastatin.

3. The method of claim 1 wherein said agent is a hydroxylation enzyme produced by said Actinomadura.

4. The method of claim 3 wherein said hydroxylation enzyme is a hydroxylase that is cytochrome P450 system-independent.

5. The method of claim 3 wherein said hydroxylation enzyme is constitutive.

6. The method of claim 1 wherein said compactin is provided by providing a microorganism that produces said compactin.

7. The method of claim 6 wherein said microorganism is selected from the group consisting of a fungus and a bacterium.

8. The method of claim 1 wherein said compactin is provided by providing a cell free extract of a microorganism that produces said compactin, said cell free extract prepared by treating whole cells of said microorganism so as to rupture said cells.

9. The method of claim 1 wherein said compactin is provided by providing cell free culture media from a pregrown culture of a microorganism that produces said compactin.

10. The method of claim 1 wherein said compactin is provided by providing a solution comprising compactin.

11. The method of claim 1 wherein said compactin is provided by providing substantially purified compactin.

12. The method of claim 1, wherein said compactin is provided in shots.

13. The method of claim 1 wherein said compactin is contacted with said agent by contacting whole cells of said Actinomadura with said compactin.

14. The method of claim 1 wherein said compactin is contacted with said agent by contacting a cell free extract of said Actinomadura with said compactin, said cell free extract prepared by treating whole cells of said Actinomadura so as to rupture said cells.

15. The method of claim 1 wherein said compactin is contacted with said agent by contacting cell free culture media from a pregrown culture of said Actinomadura with said compactin.

16. The method of claim 1 wherein said compactin is contacted with said agent by contacting a solution comprising said agent of said Actinomadura with said compactin.

17. The method of claim 6 wherein said compactin is contacted with said agent by contacting a pregrown culture of said microorganism that produces said compactin with a pregrown culture of said Actinomadura.

18. The method of claim 6 wherein said compactin is contacted with said agent by contacting a pregrown culture of said microorganism that produces said compactin with a starting culture of said Actinomadura.

19. The method of claim 6 wherein said compactin is contacted with said agent by contacting a starting culture of said microorganism that produces said compactin with a pregrown culture of said Actinomadura.

20. The method of claim 6 wherein said compactin is contacted with said agent by contacting a starting culture of said microorganism that produces said compactin with a starting culture of said Actinomadura.

21. The method of claim 6 wherein said compactin is contacted with said agent by contacting a cell free extract of said microorganism that produces said compactin with a culture of said Actinomadura.

22. The method of claim 6 wherein said compactin is contacted with said agent by contacting a culture of said microorganism that produces said compactin with a cell free extract of said Actinomadura, said cell free extract prepared by treating whole cells of said Actinomadura so as to rupture said cells.

23. The method of claim 6 wherein said compactin is contacted with said agent by contacting a cell free extract of said microorganism that produces said compactin with a cell free extract of said Actinomadura, said cell free extract of said microorganism prepared by treating whole cells of said microorganism so as to rupture said cells, and said cell free extract of said Actinomadura prepared by treating whole cells of said Actinomadura so as to rupture said cells.

24. The method of claim 1, wherein conversion of said compactin to said pravastatin is at least about 50%.

25. The method of claim 1, wherein conversion of said compactin to said pravastatin is at least about 80%.

* * * * *